United States Patent
Hou et al.

(10) Patent No.: US 11,793,435 B2
(45) Date of Patent: Oct. 24, 2023

(54) METHOD AND NON-TRANSITORY COMPUTER-READABLE STORAGE MEDIUM FOR DETECTING FOCUS OF ATTENTION

(71) Applicant: Acer Incorporated, New Taipei (TW)

(72) Inventors: Kuan-Chung Hou, New Taipei (TW); Bo-Ting Wu, New Taipei (TW); Chian-Ying Li, New Taipei (TW); Ming-Hsuan Tu, New Taipei (TW); Chien-Hung Lin, New Taipei (TW); Jian-Chi Lin, New Taipei (TW); Fu-Heng Wu, New Taipei (TW); Kai-Lun Chang, New Taipei (TW); Tsung-Yao Chen, New Taipei (TW)

(73) Assignee: ACER INCORPORATED, New Taipei (TW)

( * ) Notice: Subject to any disclaimer, the term of this patent is extended or adjusted under 35 U.S.C. 154(b) by 311 days.

(21) Appl. No.: 17/204,129

(22) Filed: Mar. 17, 2021

(65) Prior Publication Data
US 2022/0248997 A1 Aug. 11, 2022

(30) Foreign Application Priority Data
Feb. 5, 2021 (TW) .................. 110104446

(51) Int. Cl.
*A61B 5/16* (2006.01)
*A61B 5/1171* (2016.01)
(Continued)

(52) U.S. Cl.
CPC ............ *A61B 5/168* (2013.01); *A61B 5/1176* (2013.01); *A61B 5/7246* (2013.01);
(Continued)

(58) Field of Classification Search
CPC ..... A61B 5/168; A61B 5/1176; A61B 5/7246; A61B 5/7264; G06V 40/16; G06V 40/165;
(Continued)

(56) References Cited

U.S. PATENT DOCUMENTS 6,111,580 A * 8/2000 Kazama .................. G06F 3/017
715/863
7,834,912 B2  11/2010 Yoshinaga et al.
(Continued)

FOREIGN PATENT DOCUMENTS

CN       102473033 B       5/2015
CN       109829281 A       5/2019
(Continued)

OTHER PUBLICATIONS

European Search Report dated Sep. 8, 2021, issued in application No. EP 21162697.3.
(Continued)

*Primary Examiner* — Edward F Urban
*Assistant Examiner* — Wassim Mahrouka
(74) *Attorney, Agent, or Firm* — McClure, Qualey & Rodack, LLP

(57) ABSTRACT

The present disclosure provides a method for detecting the focus of attention. The method includes: obtaining the face of a person in the first image, as well as the result of facial recognition; determining whether the distance between the person and the target is within an effective attention range; determining whether the face is frontal; determining whether the effective attention period is not shorter than a period threshold; detecting the focus of attention for the person to the target.

18 Claims, 9 Drawing Sheets

(51) Int. Cl.
*A61B 5/00* (2006.01)
*G06V 40/16* (2022.01)

(52) U.S. Cl.
CPC .......... *A61B 5/7264* (2013.01); *G06V 40/16* (2022.01); *G06V 40/165* (2022.01); *G06V 40/168* (2022.01); *G06V 40/169* (2022.01); *G06V 40/173* (2022.01)

(58) Field of Classification Search
CPC .. G06V 40/168; G06V 40/169; G06V 40/173; G06V 40/171; G06V 40/172; G06V 40/18
See application file for complete search history.

(56) References Cited

U.S. PATENT DOCUMENTS

| | | | | |
|---|---|---|---|---|
| 2009/0123031 A1* | 5/2009 | Smith | .................... | A61B 5/163 348/148 |
| 2012/0169596 A1 | 7/2012 | Zhang | | |
| 2018/0024633 A1* | 1/2018 | Lo | .................... | G06F 3/1423 345/156 |
| 2018/0352150 A1* | 12/2018 | Purwar | .................... | G06T 7/194 |
| 2020/0302159 A1* | 9/2020 | Yellepeddi | .................... | H04R 3/005 |
| 2021/0026445 A1* | 1/2021 | Stoner | .................... | G06F 3/015 |
| 2021/0358252 A1* | 11/2021 | Sabripour | .................... | G06V 40/165 |
| 2022/0254158 A1* | 8/2022 | Sun | .................... | G06V 10/25 |

FOREIGN PATENT DOCUMENTS

| | | |
|---|---|---|
| CN | 110633664 A | 12/2019 |
| TW | 201812521 A | 4/2018 |

OTHER PUBLICATIONS

Jiang, Z., et al.; "i-VALS: Visual Attention Localization for Mobile Service Computing;" IEEE Access; Special Section on Mobile Service Computing with Internet of Things; vol. 7; Apr. 2019; pp. 45166-45181.

* cited by examiner

METHOD AND NON-TRANSITORY COMPUTER-READABLE STORAGE MEDIUM FOR DETECTING FOCUS OF ATTENTION

CROSS REFERENCE TO RELATED APPLICATIONS

This application claims priority of Taiwan Patent Application No. 110104446, filed on Feb. 5, 2021, the entirety of which is incorporated by reference herein.

BACKGROUND OF THE INVENTION

Field of the Invention

The present disclosure relates to a method and a non-transitory computer-readable storage medium of person behavior analysis, and more specifically it relates to a method and non-transitory computer-readable storage medium for detecting focus of attention.

Description of the Related Art

Mouse-tracking technology and eye-tracking technology are often applied in the field of person behavior analysis. For example, applied to an e-commerce website, the tracking code may be embedded behind the webpage, so as to track the mouse cursor operated by visitors (e.g., the moving trail, the standstill position, and the clicked target), thereby analyzing the browsing behavior of visitors. Through such mouse-tracking technology, the administrator of an e-commerce web site may get to know what visitors are interested in when browsing the webpage, and thereby optimize the marketing strategies or the interface of the webpage, such as determining a discount for products, adjusting the display position and the order of the products, and adjusting the size and position of various function buttons (e.g., the purchase button or the search button).

In another example, in the field of VR (virtual reality) or AR (augmented reality) gaming, features of the eyeball or the iris may be extracted by projecting light, like infrared, so as to track variations of the player's sightline, and perform a behavioral analysis. Thereby, game designers can design a more absorbing gaming experience.

As for the offline physical field, such as digital billboard advertising, product display cabinet in a physical store, and the exhibits in a business or art exhibition, tracking a person's (i.e., a customer's or a visitor's) focus of attention with reference to the cases of mouse-tracking and eyeball tracking applied in an online or virtual field, is also expected. Hence, there is a need for a method and a non-transitory computer-readable storage medium which can detect a person's focus of attention.

BRIEF SUMMARY OF THE INVENTION

The present disclosure provides a method for detecting the focus of attention, including: obtaining the face of a person in a first image, as well as the result of facial recognition of the face, wherein the result of facial recognition includes a face candidate box and a plurality of facial attributes; determining whether the distance between the person and the target is within an effective attention range based on the face candidate box; obtaining a plurality of keypoints of the face based on the face candidate box and thereby performing a frontal determination process, so as to determine whether the face is frontal, in response to the distance between the person and the target being within the effective attention range; performing an effective-attention-period calculation process based on a series of first images obtained in multiple time points in the past, so as to obtain an effective attention period for the person to the target, and thereby determining whether the effective attention period is not shorter than a period threshold, in response to the face being frontal; performing a focus-of-attention calculation process based on the target's size, the keypoints, and the face candidate box after determining that the effective attention period is not shorter than a period threshold, so as to obtain the focus of attention for the person to the target.

In some embodiments, determining whether the distance between the person and the target is within an effective attention range based on the face candidate box includes: determining whether the face candidate box's height is not smaller than an effective face size; wherein when the face candidate box's height is not smaller than the effective face size, this means that the distance between the person and the target is within the effective attention range.

In some embodiments, the effective face size is calculated by substituting the effective attention range and an FOV (field of view) into a second equation; wherein the effective attention range is calculated by substituting the target's size into a first equation; wherein the first equation and the second equation are obtained using a polynomial regression method based on a first history dataset and a second history dataset, respectively; wherein the first history dataset includes the correlation between a series of effective attention range and target's size; wherein the second history dataset includes the correlation between a series of effective face size, effective attention range, and FOV.

In some embodiments, the keypoints of the face includes a left-eye keypoint, a right-eye keypoint, a nose keypoint, a left-lips keypoint, and a right-lips keypoint.

In some embodiments, the frontal determination process includes: determining whether the nose keypoint is in a circle; determining that the face is frontal if the nose keypoint is in the circle; wherein the center of the circle is the crossing point of the first straight line between the left-eye keypoint and the right-lips keypoint and the second straight line between the right-eye keypoint and the left-lips keypoint, and the radius of the circle equals the result of a predetermined ratio multiplies the sum of the height of the face candidate box and the width of the face candidate box.

In some embodiments, the focus-of-attention calculation process includes: normalizing the circle so that the diameter of the circle is represented by 1 unit length; mapping a first location of the nose keypoint in the normalized circle to a second location in a second image corresponding to the target; wherein the second location is the focus of attention.

In some embodiments, the first location and the second location are represented in a Cartesian coordinate system; wherein mapping the first location of the nose keypoint in the normalized circle to the second location in a second image corresponding to the target includes using the following formula:

$$x = w\left(1/2\sqrt{2 + u^2 - v^2 + 2u\sqrt{2}} - 1/2\sqrt{2 + u^2 - v^2 + 2u\sqrt{2}}\right)$$

$$y = h\left(1/2\sqrt{2 - u^2 + v^2 + 2v\sqrt{2}} - 1/2\sqrt{2 - u^2 + v^2 - 2v\sqrt{2}}\right)$$

wherein (x, y) are the coordinates of the second location, (u, v) are the coordinates of the first location, w is the width of the target, and h is the height of the target.

In some embodiments, the effective-attention-period calculation process includes: obtaining a face picture by cropping the first image based on the face candidate box; obtaining a feature vector of the face picture by inputting the face picture into an AI (artificial intelligence) facial recognition model; calculating an inner product value of the feature vector and the previous feature vector, which is obtained from the previous face picture in the previous first image at the previous time point; determining whether the face picture and the previous face picture belong to the same person based on the inner product value; calculating the effective attention period for the person to the target based on a series of time points corresponding to a series of face pictures belonging to the same person.

The present disclosure also provides a non-transitory computer-readable storage medium storing program for detecting the focus of attention, wherein the program causes a computer to execute: causing a processor to obtain the face of a person in a first image, as well as the result of facial recognition, wherein the result of facial recognition includes a face candidate box and a plurality of facial attributes; causing the processor to determine whether the distance between the person and the target is within an effective attention range based on the face candidate box; causing the processor to obtain a plurality of keypoints based on the face candidate box and thereby performing a frontal determination process, so as to determine whether the face is frontal, in response to the distance between the person and the target being within the effective attention range; causing the processor to perform an effective-attention-period calculation process based on a series of first images to obtain an effective attention period for the person to the target, and thereby determining whether the effective attention period is not shorter than a period threshold, in response to the face being frontal; causing the processor to perform a focus-of-attention calculation process based on the target's size, the keypoints, and the face candidate box after determining that the effective attention period is not shorter than a period threshold, so as to obtain the focus of attention for the person to the target.

In some embodiments, regarding the non-transitory computer-readable storage medium for detecting the focus of attention, the program causes the computer to further execute: causing the processor to verify whether the face is effectively paying attention to the target by using a machine learning classification model based on the facial attributes and a plurality of target attributes of the target, in response to the effective attention period not being shorter than the period threshold; wherein performing the focus-of-attention calculation process based on the target's size, the keypoints, and the face candidate box after determining that the effective attention period is not shorter than a period threshold includes: performing the focus-of-attention calculation process based on the target's size, the keypoints, and the face candidate box in response to the face being effective.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

The present disclosure provides a method and a non-transitory computer-readable storage medium for detecting the focus of attention. Depending on the application scenarios, there may be various types of persons and targets. For example, in the application scenario of digital billboard advertising, the person is a passenger passing by the digital billboard, the target is the digital billboard, and the present disclosure may be used for detecting the passenger's focus of attention is at which regions (e.g., the upper left region or the lower right region) on the digital billboards. In the application scenario of physical stores, the person is a customer of the store, the target is the product display cabinet, and the present disclosure may be used for detecting the customer's focus of attention is at which products on the product display cabinet. In the application scenario of business or art exhibitions, the person is a visitor of the exhibition, the target are multiple exhibits, and the present disclosure may be used for detecting the visitor's focus of attention is at which exhibits among the multiple exhibits described above. However, the persons and the targets described by the present disclosure are not limited to the examples presented above.

Figure 1:
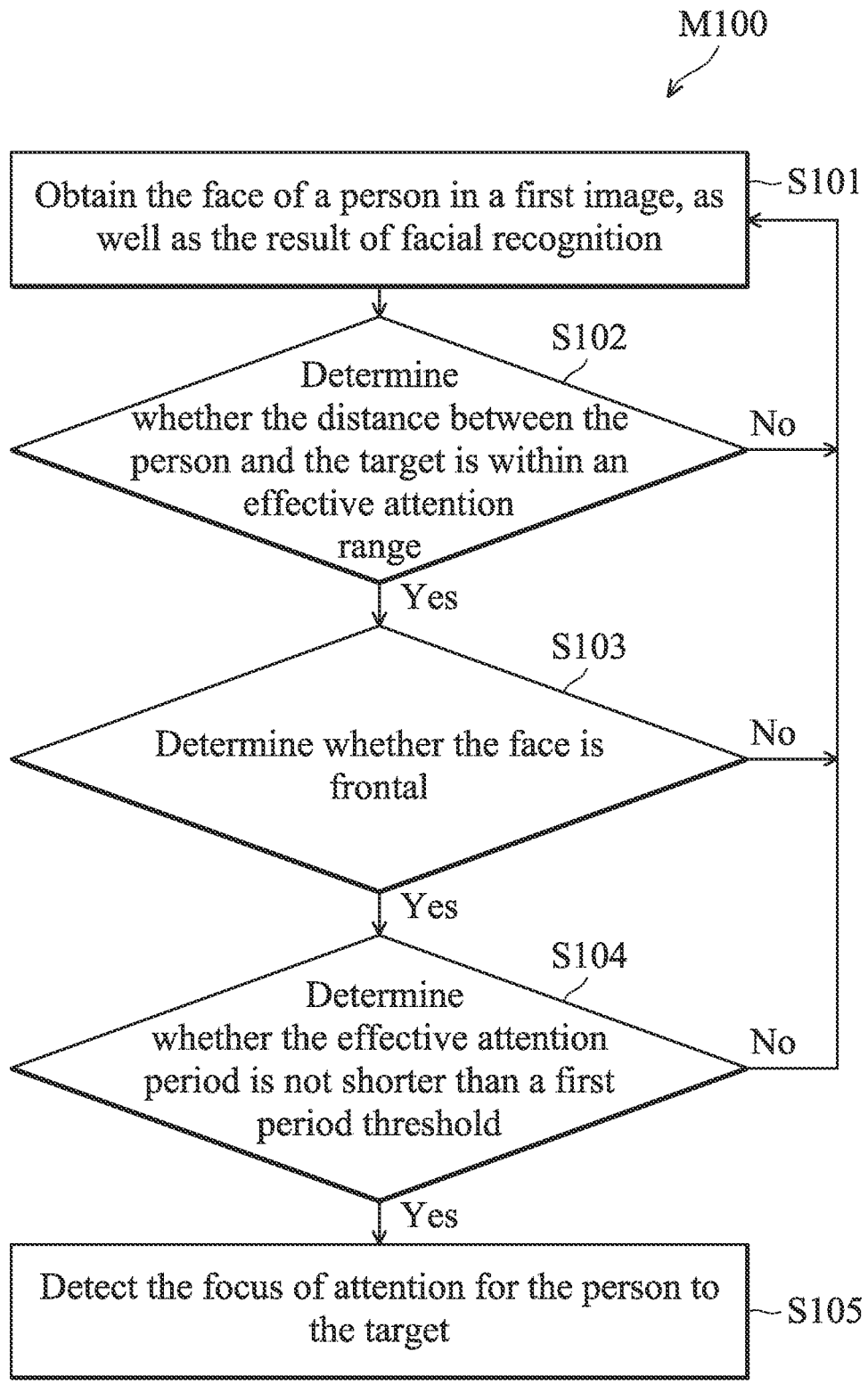
FIG. 1 illustrates the flow diagram of a method M100 for detecting the focus of attention, according to the embodiments of the present disclosure.

FIG. 1 illustrates the flow diagram of a method M100 for detecting the focus of attention, according to the embodiments of the present disclosure. As shown in FIG. 1, the method 100 includes steps S101-S105.

The method M100 starts from step S101. In step S101, obtain the face of a person in a first image, as well as the result of facial recognition. The result of facial recognition may be obtained using any common algorithm for facial recognition. The present disclosure is not limited thereto. Then, the method M100 enters step S102.

In some embodiment of the present disclosure, the first image is captured with the viewpoint from the target to the persons by using a photographic device. For example, in the application scenario of digital billboard advertising, the photographic device may be installed above the center point of the digital billboard to capture a passenger passing by the digital billboard as the first image. In the application scenario of physical stores, the photographic device may be installed above the center point of the product display cabinet to capture a customer in front of the product display cabinet as the first image. In the application scenario of business or art exhibitions, the photographic device may be installed above the center point of multiple exhibits to capture a visitor of the exhibition as the first image. However, in some embodiment of the present disclosure, the installation of the photographic device is not limited to the examples presented above. In the examples presented above and other examples, the photographic device may include a camera lens to aid in capturing images, and the camera lens includes a common optical lens or an infrared lens. The type and the quantity of the camera lenses are not limited in the present disclosure.

In the embodiments of the present disclosure, the result of facial recognition includes a face candidate box and a plurality of facial attributes. The face candidate box indicates the position and the size of the face in the first image by using a rectangular area enclosing the face. The facial attributes may include, for example, the attributes for representing the person's profiles, such as gender, age, and emotion.

Figure 2:
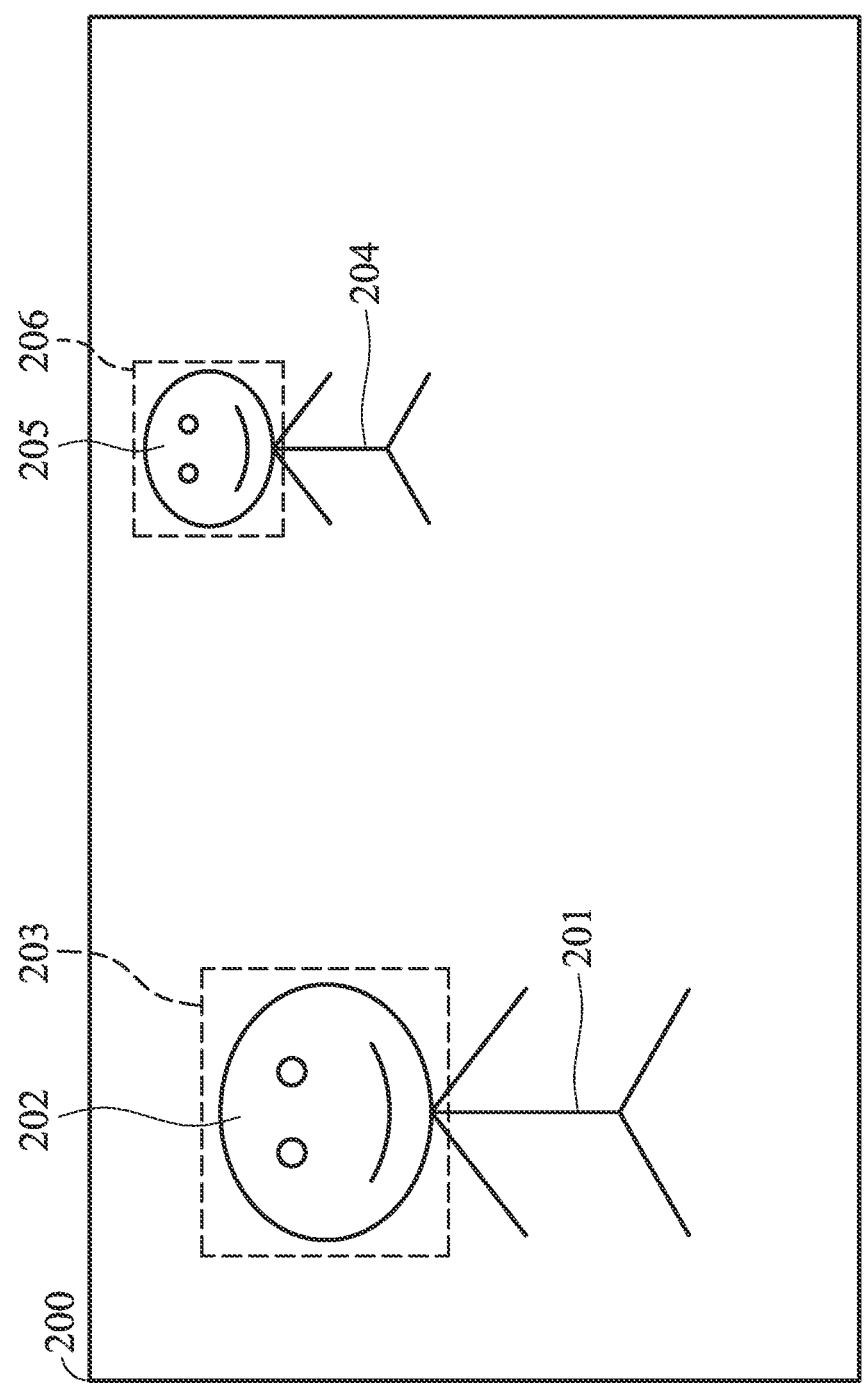
FIG. 2 illustrates the schematic diagram of an example of the first image 200, according to the embodiments of the present disclosure.

FIG. 2 illustrates the schematic diagram of an example of the first image 200, according to the embodiments of the present disclosure. As shown in FIG. 2, the first image 200 includes a person 201, a person 204, a face 202 which belongs to the person 201, a face 205 which belongs to the person 204, a face candidate box 203 enclosing the face 202, and a face candidate box 206 enclosing the face 205. In the example illustrated by FIG. 2, it is assumed that the person 201 is closer to the target (no shown in FIG. 2), so the size of the face 202 will be bigger than the size of the face 205. Correspondingly, the size of the face candidate box 203 will also be bigger than the size of the face candidate box 206. In addition, it should be noted that even though the face 202 and the face 205 illustrated in FIG. 2 look completely frontal, but in fact the faces in the first image may have an angle of rotation. The issue regarding determining whether a face is frontal will be discussed hereinafter.

Back to FIG. 1, the method M100 now proceeds to step S102. In step S102, a determination is made whether the distance between the person and the target is within an effective attention range based on the face candidate box. If the distance between the person and the target is within the effective attention range, enter step S103. If the distance between the person and the target exceeds the effective attention range, return to step S101 to continue the calculation for other persons' focus of attention. The purpose of step S102 is to exclude the persons in the first image who are too far from the target. Since these persons are too far from the target, they are probably not paying attention to the target, so they don't need to be taken into account for the subsequent calculation of the focus of attention.

In some embodiments, step S102 determines whether the distance between the person and the target is within the effective attention range by determining whether the face candidate box's height is not smaller than an effective face size. If the face candidate box's height is not smaller than the effective face size, this means that the distance between the person and the target is within the effective attention range. Otherwise, if the face candidate box's height is smaller than the effective face size, this means that the distance between the person and the target exceeds the effective attention range.

In some embodiments, the effective face size is calculated by substituting the effective attention range and the photographic device's FOV (field of view) into a second equation, and the effective attention range is calculated by substituting the target's size into a first equation. In other words, substitute the target's size into the first equation, and then substitute the effective attention range and the photographic device's FOV into the second equation, so as to get the effective face size.

Figure 3:
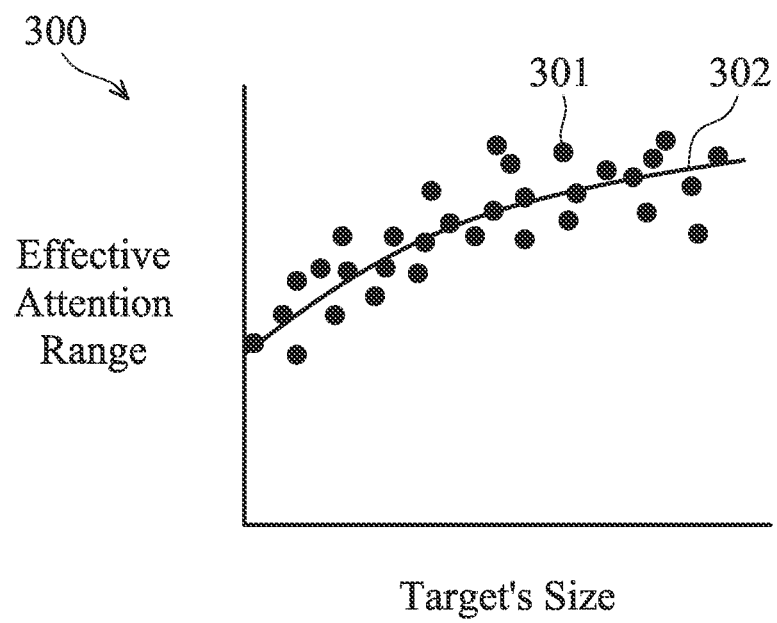
FIG. 3 illustrates a coordinate system 300 displaying a first equation 302, according to the embodiments of the present disclosure.

FIG. 3 illustrates a coordinate system 300 displaying a first equation 302, according to the embodiments of the present disclosure. As shown in FIG. 3, the horizontal axis and the vertical axis of the coordinate system 300 represent the target's size and the effective attention range respectively. The first equation 302 may be displayed in the form of a straight line or a curve in the coordinate system 300, to represent the correlation between target's size and the effective attention range.

In some embodiments, the first equation 302 is obtained using a polynomial regression method based on a first history dataset. The first history dataset includes a series of history data 301 (as shown in FIG. 3) to represent the correlation between a series of effective attention range and target's size. For example, in the application scenario of digital billboard advertising, let's assume that when digital billboard's size is 30 inches, 50 inches, 70 inches and so on, the effective attention range is 1 meter, 1.8 meters, 2.4 meters and so on, according to knowledge, experience or experimental results in the past. Thus the exemplary correlations (30 inches, 1 meter), (50 inches, 1.8 meters), (70 inches, 2.4 meters) and so on may be subsumed under a series of history data 301, so as to calculate the first equation 302.

Figure 4:
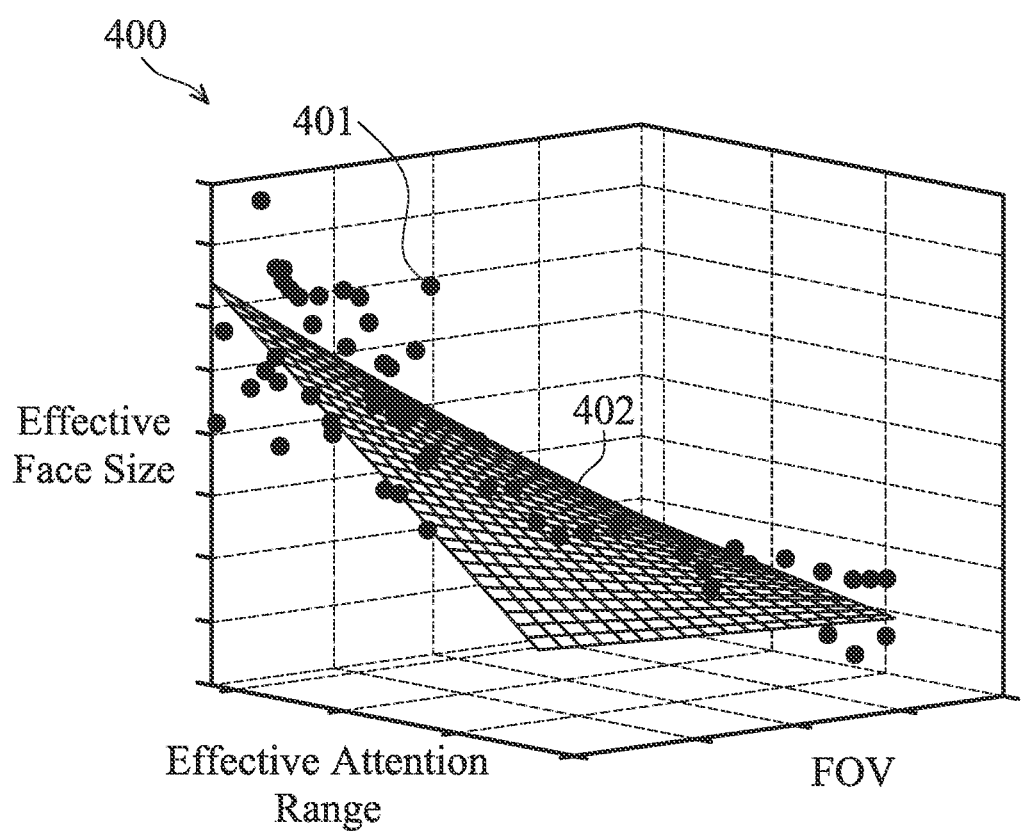
FIG. 4 illustrates a coordinate system 400 displaying a second equation 402, according to the embodiments of the present disclosure.

FIG. 4 illustrates a coordinate system 400 displaying a second equation 402, according to the embodiments of the present disclosure. As shown in FIG. 4, the x-axis, the y-axis, and the z-axis represent the photographic device's FOV, the effective attention range, and the effective face size. The second equation 402 may be displayed in the form of a plane or a curved surface in the coordinate system 402, to represent the correlation between the photographic device's FOV, the effective attention range, and the effective face size.

In some embodiments, the second equation 402 is obtained using the polynomial regression method based on a second history dataset. The second history dataset includes a series of history data 401 (as shown in FIG. 4) to represent the correlation between a series of the camera's FOV the effective attention range, and the effective face size. For example, in the application scenario of digital billboard advertising, let's assume that when the photographic device's FOV is 90 degrees and the effective attention range is 1.5 meters, the effective face size is 130 pixels; when the photographic device's FOV is 78 degrees and the effective attention range is 2 meters, the effective face size is 100 pixels, according to knowledge, experience, or experimental results in the past. Thus the exemplary correlations (90 degree, 1.5 meter, 130 pixel), (78 degree, 2 meter, 100 pixel) and the like may be subsumed under a series of history data 401, so as to calculate the second equation 402.

Back to FIG. 1, the method M100 now proceeds to step S103. In step S103, obtain a plurality of keypoints based on the face candidate box and thereby performing a frontal determination process, so as to determine whether the face is frontal. If the face is frontal, enter step S104. If the face is not frontal, enter step S101 to continue the calculation for other persons' focus of attention. The purpose of step S103 is to exclude the persons in the first image whose face's angle of rotation is too large for the target. Since their face's angle of rotation is too large, they are probably not paying attention to the target, so they don't need to be taken into account for the subsequent calculation of the focus of attention.

In some embodiments, the keypoints includes a left-eye keypoint, a right-eye keypoint, a nose keypoint, a left-lips keypoint, and a right-lips keypoint. The keypoints may be obtained using any common algorithm for facial landmark detection. The present disclosure is not limited thereto.

Figure 5:
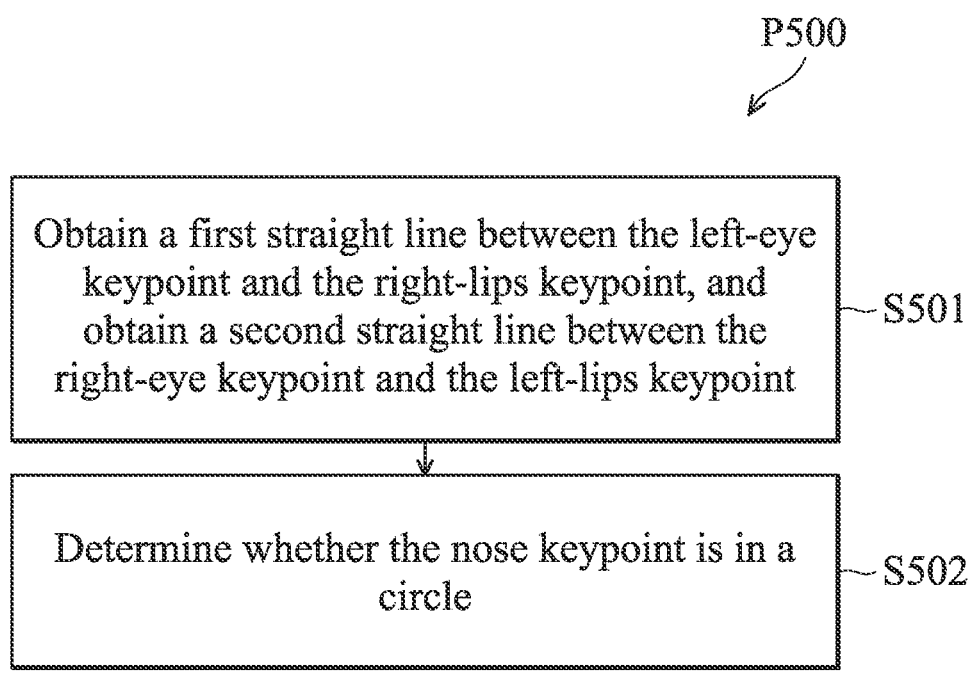
FIG. 5 illustrates the flow diagram of a frontal determination process P500 performed in step S103, according to the embodiments of the present disclosure.
Figure 6:
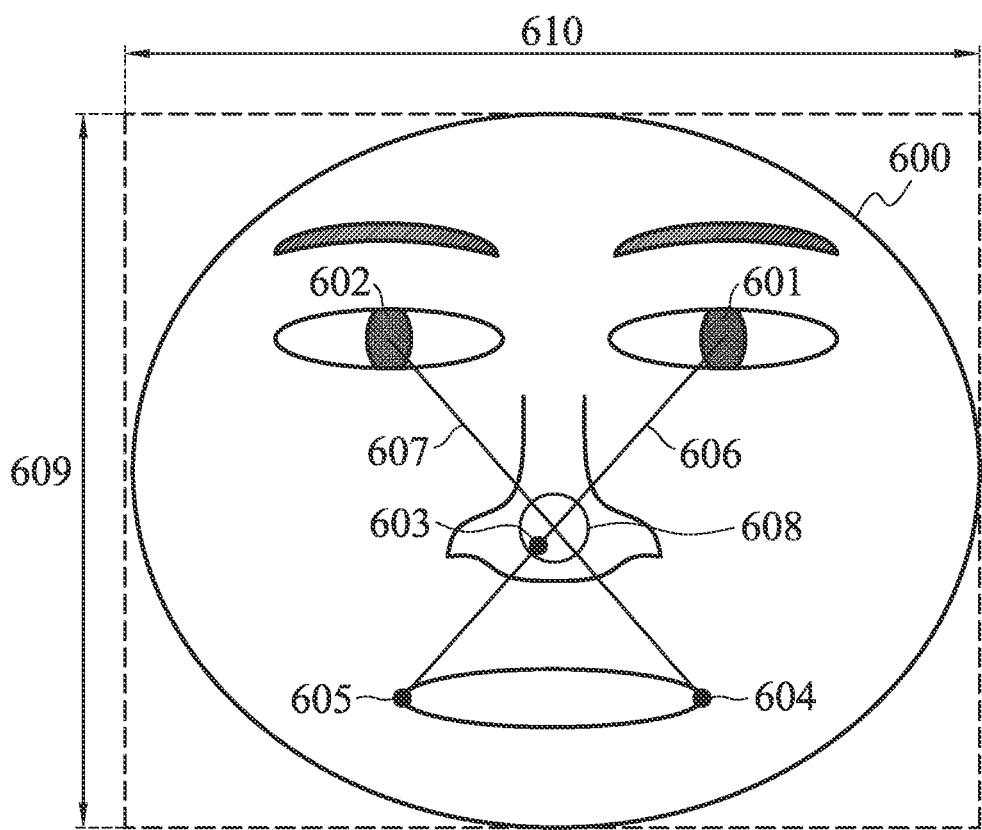
FIG. 6 illustrates the schematic diagram of the frontal determination process P500, according to the embodiments of the present disclosure.

FIG. 5 illustrates the flow diagram of a frontal determination process P500 performed in step S103, according to the embodiments of the present disclosure. As shown in FIG. 5, the frontal determination process P500 includes a step S501 and a step S502. FIG. 6 illustrates the schematic diagram of the frontal determination process P500, according to the embodiments of the present disclosure. Please refer to FIG. 5, FIG. 6, and the description hereinafter together to better understand the embodiments of the present disclosure.

The frontal determination process P500 starts from step S501. In step S501, as shown in FIG. 6, obtain a first straight line 606 between the left-eye keypoint 601 and the right-lips keypoint 605 of a face 600, and obtain a second straight line 607 between the right-eye keypoint 602 and the left-lips keypoint 604 of the face 600. Then, the frontal determination process P500 enters step S502.

In step S502, as shown in FIG. 6, a determination is made whether the nose keypoint 603 is in a circle 608. If the nose keypoint 603 is in the circle 608, this means that the face 600 is frontal. The center of the circle 608 is the crossing point of the first straight line 606 and the second straight line 607, and the radius of the circle 608 equals the result of a predetermined ratio multiplies the sum of the face candidate box's height 609 and the face candidate box's width 610. In a preferred embodiment, the predetermined ratio is 0.0045.

Back to FIG. 1, the method M100 now proceeds to step S104. In step S104, perform an effective-attention-period calculation process based on a series of first images obtained in multiple time points in the past to obtain an effective attention period for the person to the target, and thereby determine whether the effective attention period is not shorter than a first period threshold (e.g., 10 seconds, but the present disclosure is not limited thereto). If the effective attention period is not shorter than the first period threshold, enter step S105. If the effective attention period is shorter than the first period threshold, return to step S101 to continue the calculation for other persons' focus of attention. The purpose of step S104 is to exclude the persons in the first image who has been paying attention to the target for not long enough. Even though these persons are close enough to the target and their face are frontal for the target, it could be just a quick glance. Whether they are paying attention to the target cannot be sure yet, so for the time being they don't need to be taken into account for the subsequent calculation of the focus of attention.

Figure 7:
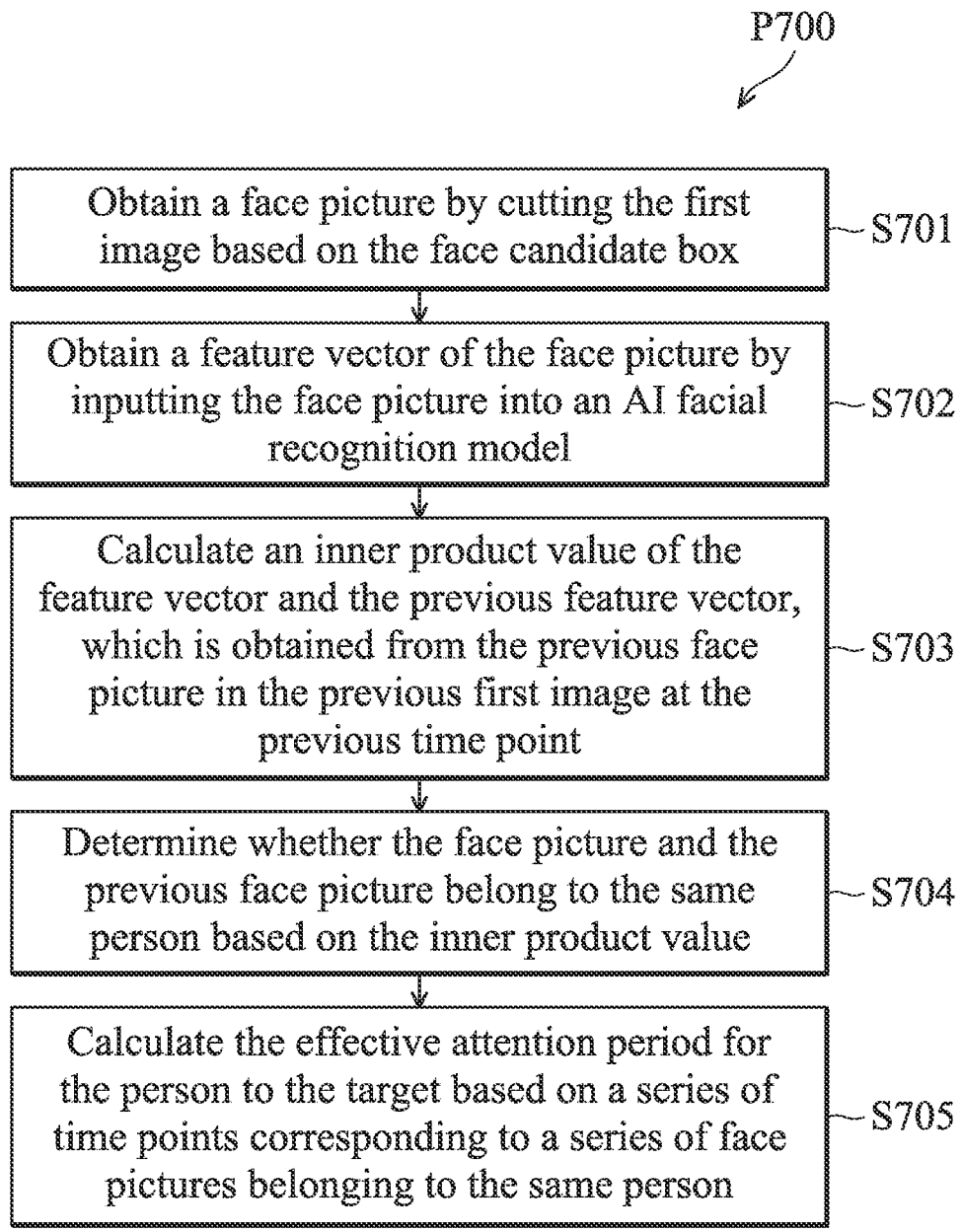
FIG. 7 illustrates the flow diagram of an effective-attention-period calculation process P700 performed in step S104, according to the embodiments of the present disclosure.

FIG. 7 illustrates the flow diagram of an effective-attention-period calculation process P700 performed in step S104, according to the embodiments of the present disclosure. As shown in FIG. 7, the effective-attention-period calculation process P700 includes steps S701-S705.

The effective-attention-period calculation process P700 starts from step S701. In step S701, obtain a face picture by cropping the first image based on the face candidate box. Then, the effective-attention-period calculation process P700 enters step S702.

In step S702, obtain a feature vector of the face picture by inputting the face picture into an AI (artificial intelligence) facial recognition model. Then, the effective-attention-period calculation process P700 enters step S703. The AI facial recognition model may be any common techniques of feature extraction based on CNN (Convolutional Neural Network), but the present disclosure is not limited thereto. The feature vector is a unit vector having multiple dimensions, for representing the features of the face. In a preferred embodiment, the feature vector has 128 dimensions.

In step S703, calculate an inner product value of the feature vector and the previous feature vector, which is obtained from the previous face picture in the previous first image at the previous time point. Then, the effective-attention-period calculation process P700 enters step S704. The inner product value is for representing the similarity between the feature vector and the previous feature vector. When the inner product is closer to 1, this means that the feature vector is more similar to the previous feature vector.

In step S704, a determination is made whether the face picture and the previous face picture belong to the same person based on the inner product value calculated in the previous step. Specifically, if the inner product reaches a predetermined inner product threshold, a determination is made that the face picture and the previous face picture belong to the same person. Then, the effective-attention-period calculation process P700 enters step S705.

In a preferred embodiment, in step S704, a calculation is further performed on the overlap of the face picture and the previous face picture whose inner product value has not reached the inner product threshold. If the overlap of the face picture and the previous face picture reaches a predetermined overlap threshold, determines that the face picture and the previous face picture belong to the same person, even though the inner product value has not reached the inner product threshold.

In step S705, calculate the effective attention period for the person to the target based on a series of time points corresponding to a series of face pictures belonging to the same person. For example, assuming that a series of face candidate boxes that correspond to a series of time points in the past almost 30 seconds (e.g., if in the unit of seconds, there will be 30 time points, the first second, the second second, the third second, etc., but the present disclosure is not limited thereto) are determined to belong to the same person, then the effective attention period is 30 seconds. Accordingly, in step S104 in FIG. 1, whether the effective attention period (30 seconds in this example) is not shorter than the first period threshold (e.g., 10 seconds, but the present disclosure is not limited thereto) may be determined.

In some embodiments, a second period threshold (e.g., 5 seconds, but the present disclosure is not limited thereto) allowed for the focus of attention leaving the target may be configured depending on the actual demands. As the example presented in the previous paragraph, assuming that the face candidate boxes during the period from the 20$^{th}$ second to the 23$^{rd}$ second are not determined to belong to the same person. This could be because that the person temporarily goes beyond the effective attention range from the target, or could be because that the person temporarily turns his/her head so that his/her face is not determined to be frontal during this 3 second period. If the second period threshold is configured to be 5 seconds, the effective attention period is determined to be 30 seconds, as the focus of attention temporarily leaves the target for 3 seconds, which is shorter than the second period threshold of 5 seconds. If the second period threshold is configured to be 2 seconds, it is determined that the effective attention period will be 20 seconds, as the focus of attention temporarily leaves the target for 3 seconds, which is longer than the second period threshold of 2 seconds.

Back to FIG. 1, the method M100 now proceeds to step S105. In step S105, perform a focus-of-attention calculation process based on the target's size, the keypoints (e.g., the left-eye keypoint 601, the right-eye keypoint 602, the nose keypoint 603, the left-lips keypoint 604, and the right-lips keypoint 605), and the face candidate box, so as to obtain the focus of attention for the person to the target.

Figure 8:
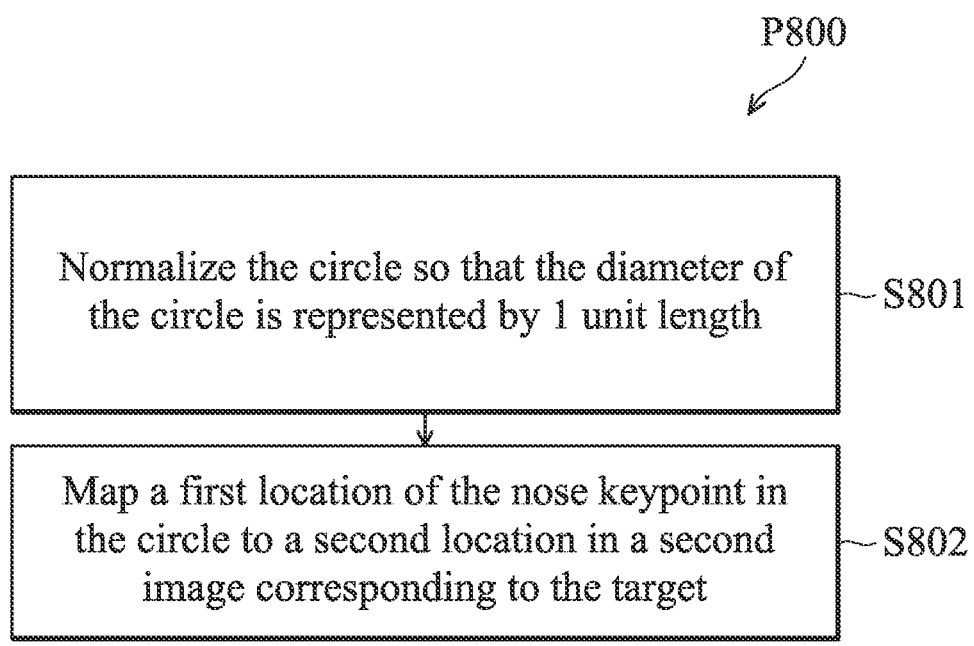
FIG. 8 illustrates the flow diagram of a focus-of-attention calculation process P800 performed in step S105, according to the embodiments of the present disclosure.

FIG. 8 illustrates the flow diagram of a focus-of-attention calculation process P800 performed in step S105, according to the embodiments of the present disclosure. As shown in FIG. 8, the focus-of-attention calculation process P800 includes a step S801 and a step S802.

The focus-of-attention calculation process P800 starts from step S801. In step S801, normalize the circle 608 in FIG. 6 so that the diameter of the circle 608 is represented by 1 unit length. Then, the focus-of-attention calculation process P800 enters step S802.

In step S802, map a first location of the nose keypoint 603 in the circle 608 in FIG. 6 to a second location in a second image corresponding to the target. The second location is the focus of attention.

In the embodiments of the present disclosure, the second image simulates the view saw by a person facing the target. For example, in the application scenario of digital billboard advertising, the second image may be the view on the digital billboard saw by a passenger passing by the digital billboard, that is, the content being displayed by the digital billboard. In the application scenario of the physical stores, the second image may be captured from the viewpoint of a customer in front of the product display cabinet to the product display cabinet. In the scenario of business or art exhibitions, the second image may be captured from the viewpoint of a visitor of the exhibition to the multiple exhibits.

Figure 9A:
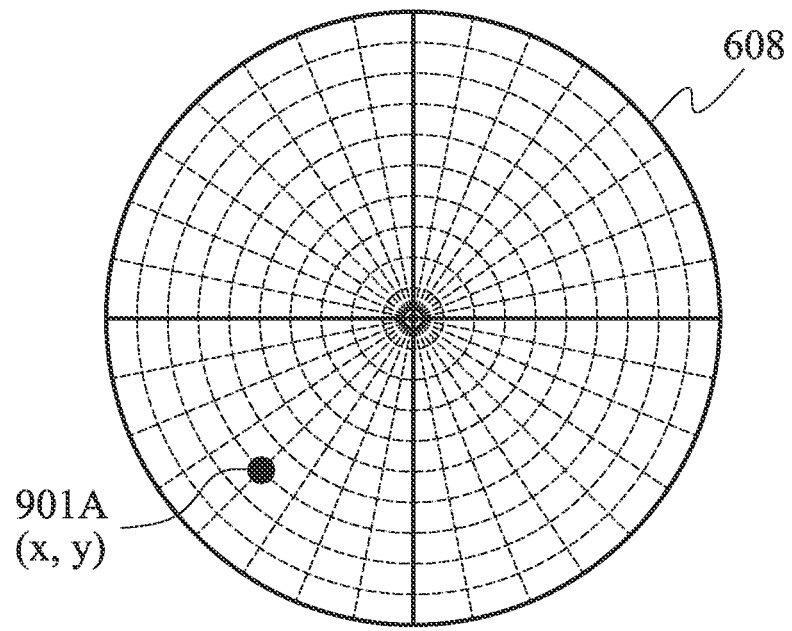
FIG. 9A illustrates an exemplary first location 901A of the nose keypoint 603 in the circle 608, according to the embodiments of the present disclosure.
Figure 9B:
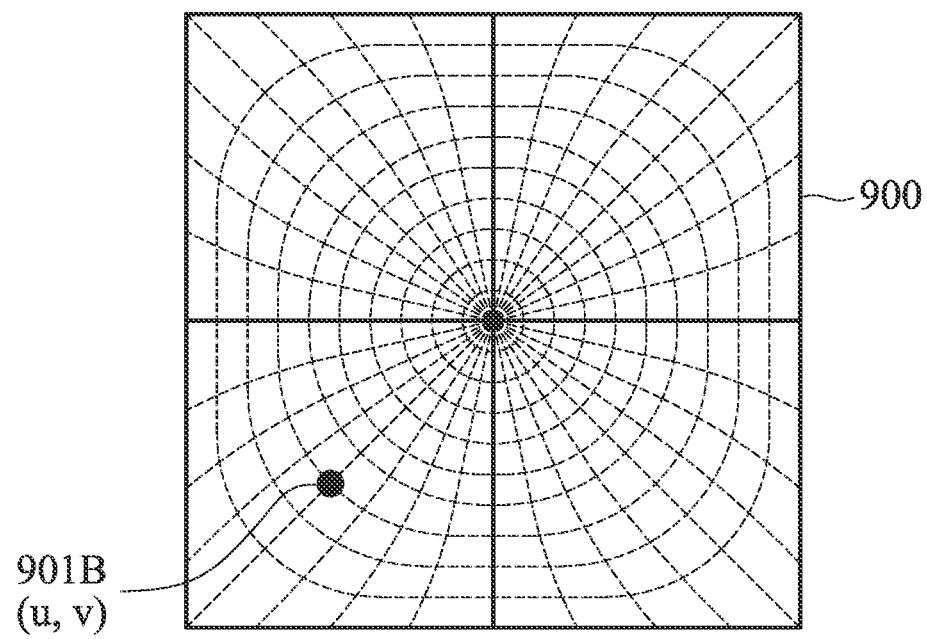
FIG. 9B illustrates an exemplary second location 901B (i.e., the focus of attention) in a second image 900 to which the first location 901A is mapped after performing the focus-of-attention calculation process P800, according to the embodiments of the present disclosure.

FIG. 9A illustrates an exemplary first location 901A of the nose keypoint 603 in the circle 608, according to the embodiments of the present disclosure. Correspondingly, FIG. 9B illustrates an exemplary second location 901B (i.e., the focus of attention) in a second image 900 to which the first location 901A is mapped after performing the focus-of-attention calculation process P800, according to the embodiments of the present disclosure.

In some embodiments, the first location 901A may be represented in a Cartesian coordinate system. For example, in FIG. 9A, the origin of the Cartesian coordinate system is the circle 608, and the diameter of the circle 608 is 1 unit length, so the coordinates (x, y) of the first location 901A can be obtained. Then, the coordinates (x, y) of the first location 901A may be mapped to the coordinates (u, v) of the second location 901B in the second image 900 using the following formula:

$$x = w\left(1/2\sqrt{2+u^2-v^2+2u\sqrt{2}} - 1/2\sqrt{2+u^2-v^2+2u\sqrt{2}}\right)$$

$$y = h\left(1/2\sqrt{2-u^2+v^2+2v\sqrt{2}} - 1/2\sqrt{2-u^2+v^2-2v\sqrt{2}}\right)$$

wherein w is the width of the target, and h is the height of the target.

Figure 10:
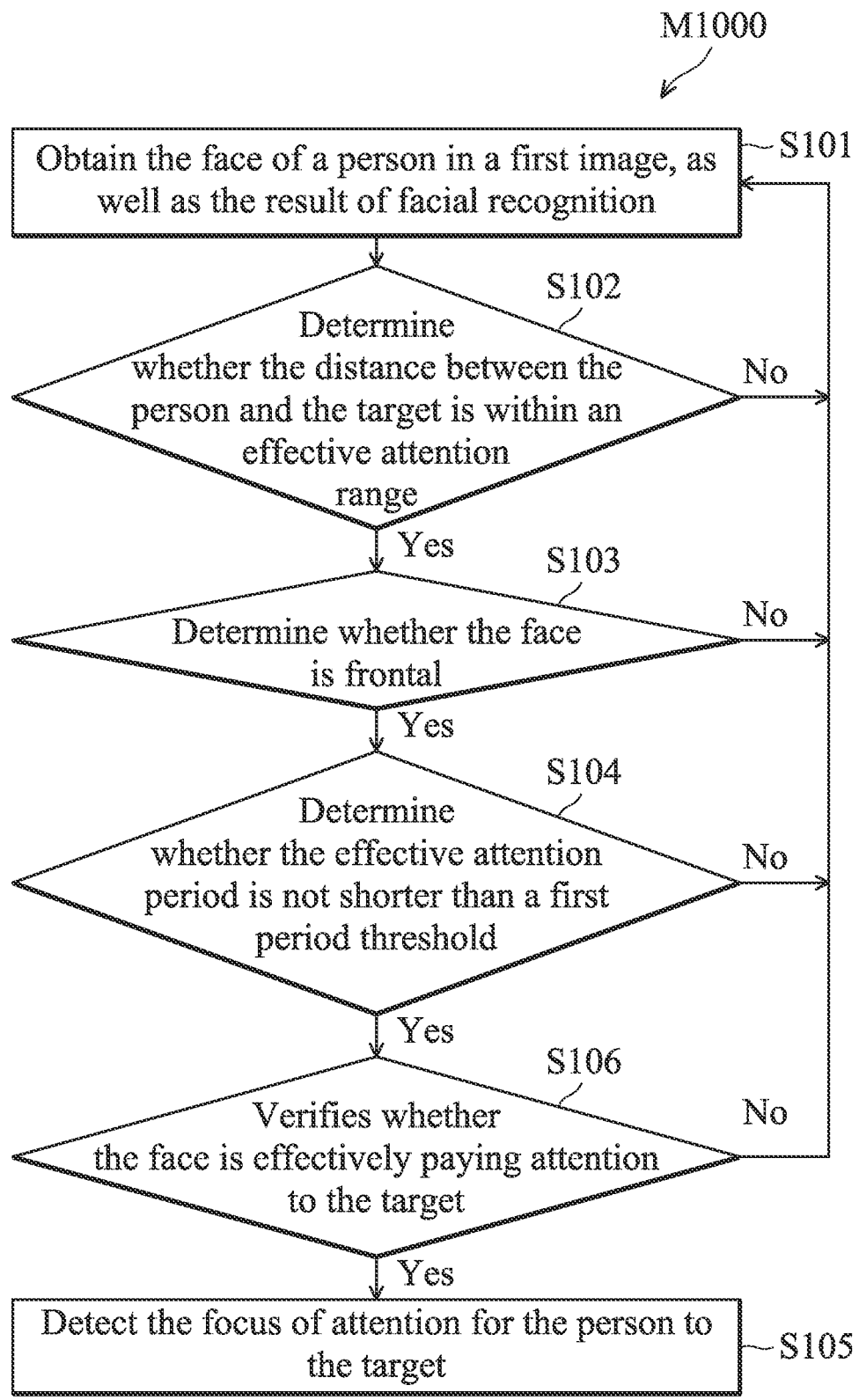
FIG. 10 illustrates the flow diagram of a method M1000 for detecting the focus of attention, according to a preferred embodiment of the present disclosure.

FIG. 10 illustrates the flow diagram of a method M1000 for detecting the focus of attention, according to a preferred embodiment of the present disclosure. As shown in FIG. 10, the method M1000 inserts a step S106 between step S104 and step S105, compared to the method M100 illustrated in FIG. 1.

In a preferred embodiment, if the effective attention period is determined to be longer than the period threshold in step S104, step S106 is performed. Step S106 further verifies whether the face is effectively paying attention to the target by using a machine learning classification model based on the facial attributes (e.g., sex, gender, and emotion) and a plurality of target attributes (e.g., the content and the time length of the digital billboard advertisement, the category and the price of the product displayed on the product display cabinet, etc.) of the target. If the face is determined to be effective, enter step S105. If the face is determined to be not effectively paying attention to the target, return to step S101 to continue the calculation for other persons' focus of attention. The purpose of step S106 is to further select the faces that need to be taken into account for the subsequent calculation of the focus of attention according to the facial attributes and the target attributes, so as to make the calculation of the focus of attention more effective and accurate.

In a preferred embodiment, the machine learning classification model used in step S105 may be any classifier based on CNN (Convolutional Neural Network), but the present disclosure is not limited thereto. The data required for training the classification model may be a series of history data recording correlations between the face attributes and the target attributes.

Regarding the non-transitory computer-readable storage medium provided by the present disclosure, the program is loaded by a computer to execute step S101-S105 in FIG. 1 or FIG. 10. In preferred embodiments, the stored program in the non-transitory computer-readable storage medium further causes the processor to execute step S106 in FIG. 10.

In the embodiments of the present disclosure, the processor may be any device used for executing instructions, such as a CPU (central processing unit), a microprocessor, a controller, a microcontroller, or a state machine.

The method and the non-transitory computer-readable storage medium provided by the present disclosure may be applied in the offline physical filed to find out the focus of attention for a person to the target. For example, in FIG. 9B, the second location 901B (i.e., the focus of attention) is at the lower left region of the second image 900. In the application scenario of digital billboard advertising, the result as shown by FIG. 9B may represent a person's focus of attention being in the lower left region of the digital billboard. In the application scenario of physical stores, the result as shown by FIG. 9B may represent a customer's focus of attention being on the products in the lower left region of the product display cabinet. In the application scenario of business or art exhibitions, the result as shown by FIG. 9B may represent a visitor's focus of attention being on the exhibits that are placed in the lower left corner. Through accumulating large amount of people's focus of attention, the distribution of these people's focus of attention may be illustrated using a heat map, so as to help decision makers improve their marketing or display strategies.

The order numbers in the specification and claims, such as "the first", "the second" and the like, are only for the convenience of description. There are no chronological relationships between these order numbers.

"Some Embodiments", "An Embodiment", "Embodiment", "Embodiments", "This Embodiment", "These Embodiments", "One or More Embodiments", "Some of the embodiments" and the "one embodiment" mean one or more embodiments, but not all, unless otherwise specifically defined.

The above paragraphs are described with multiple aspects. Obviously, the teachings of the specification may be performed in multiple ways. Any specific structure or function disclosed in examples is only a representative situation. According to the teachings of the specification, it should be noted by those skilled in the art that any aspect disclosed may be performed individually, or that more than two aspects could be combined and performed.

While the invention has been described by way of example and in terms of the preferred embodiments, it should be understood that the invention is not limited to the disclosed embodiments. Rather, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A computer-implemented method for detecting a focus of attention, comprising:
    obtaining a face of a person in a first image, as well as the result of facial recognition of the face, wherein the result of facial recognition comprises a face candidate box and a plurality of facial attributes;
    determining whether a distance between the person and a target is within an effective attention range based on the face candidate box;
    obtaining a plurality of keypoints of the face based on the face candidate box and performing a frontal determination process according to the keypoints, so as to determine whether the face is frontal, in response to the distance between the person and the target being within the effective attention range;
    performing an effective-attention-period calculation process based on a series of first images obtained in multiple time points in the past, so as to obtain an effective attention period for the person to the target, and thereby determining whether the effective attention period is not shorter than a period threshold, in response to the face being frontal; and
    performing a focus-of-attention calculation process based on the target's size, the keypoints, and the face candidate box after determining that the effective attention period is not shorter than a period threshold, so as to obtain the focus of attention for the person to the target.

2. The method as claimed in claim 1, wherein determining whether the distance between the person and the target is within an effective attention range based on the face candidate box comprises:
    determining whether the face candidate box's height is not smaller than an effective face size;
    determining the distance between the person and the target is within the effective attention range in response to detecting that the face candidate box's height not being smaller than the effective face size.

3. The method as claimed in claim 2, wherein the effective face size is calculated by substituting the effective attention range and an FOV (field of view) into a second equation;
    wherein the effective attention range is calculated by substituting the target's size into a first equation;
    wherein the first equation and the second equation are obtained using a polynomial regression method based on a first history dataset and a second history dataset, respectively;
    wherein the first history dataset comprises the correlation between a series of effective attention range and target's size;
    wherein the second history dataset comprises a correlation between a series of effective face size, effective attention range, and FOV.

4. The method as claimed in claim 1, wherein the keypoints of the face comprise a left-eye keypoint, a right-eye keypoint, a nose keypoint, a left-lips keypoint, and a right-lips keypoint.

5. The method as claimed in claim 4, wherein the frontal determination process comprises:
    determining whether the nose keypoint is in a circle;
    determining that the face is frontal if the nose keypoint is in the circle;
    wherein the center of the circle is the crossing point of the first straight line between the left-eye keypoint and the right-lips keypoint and the second straight line between the right-eye keypoint and the left-lips keypoint, and the radius of the circle equals the result of a predetermined ratio multiplies the sum of the height of the face candidate box and the width of the face candidate box.

6. The method as claimed in claim 5, wherein the focus-of-attention calculation process comprises:
    normalizing the circle so that the diameter of the circle is represented by 1 unit length;
    mapping a first location of the nose keypoint in the normalized circle to a second location in a second image corresponding to the target;
    wherein the second location is the focus of attention.

7. The method as claimed in claim 6, wherein the first location and the second location are represented in the form of Cartesian coordinate system; and
    wherein mapping the first location of the nose keypoint in the normalized circle to the second location in a second image corresponding to the target comprises using the following formula:

$$x = w\left(1/2\sqrt{2 + u^2 - v^2 + 2u\sqrt{2}} - 1/2\sqrt{2 + u^2 - v^2 + 2u\sqrt{2}}\right)$$
$$y = h\left(1/2\sqrt{2 - u^2 + v^2 + 2v\sqrt{2}} - 1/2\sqrt{2 - u^2 + v^2 - 2v\sqrt{2}}\right)$$

wherein (x, y) are the coordinates of the second location, (u, v) are the coordinates of the first location, w is the width of the target, and h is the height of the target.

8. The method as claimed in claim 1, wherein the effective-attention-period calculation process comprises:
    obtaining a face picture by cropping the first image based on the face candidate box;
    obtaining a feature vector of the face picture by inputting the face picture into an AI (artificial intelligence) facial recognition model;
    calculating an inner product value of the feature vector and a previous feature vector, which is obtained from a previous face picture in a previous first image at a previous time point;

determining whether the face picture and the previous face picture belong to the same person based on the inner product value;

calculating the effective attention period for the person to the target based on a series of time points corresponding to a series of face pictures belonging to the same person.

9. The method as claimed in claim 1, further comprising:

verifying whether the face is effectively paying attention to the target by using a machine learning classification model based on the facial attributes and a plurality of target attributes of the target, in response to the effective attention period not being shorter than the period threshold;

wherein performing the focus-of-attention calculation process based on the target's size, the keypoints, and the face candidate box after determining that the effective attention period is not shorter than a period threshold comprises:

performing the focus-of-attention calculation process based on the target's size, the keypoints, and the face candidate box in response to the face being effective.

10. A non-transitory computer-readable storage medium storing program which causes a computer to execute:

causing a processor to obtain the face of a person in a first image, as well as the result of facial recognition of the face, wherein the result of facial recognition comprises a face candidate box and a plurality of facial attributes;

causing the processor to determine whether a distance between the person and the target is within an effective attention range based on the face candidate box;

causing the processor to obtain a plurality of keypoints of the face based on the face candidate box and performing a frontal determination process according to the keypoints, so as to determine whether the face is frontal, in response to the distance between the person and the target being within the effective attention range;

causing the processor to perform an effective-attention-period calculation process based on a series of first images obtained in multiple time points in the past, so as to obtain an effective attention period for the person to the target, and thereby determining whether the effective attention period is not shorter than a period threshold, in response to the face being frontal;

causing the processor to perform a focus-of-attention calculation process based on the target's size, the keypoints, and the face candidate box after determining that the effective attention period is not shorter than a period threshold, so as to obtain the focus of attention for the person to the target.

11. The non-transitory computer-readable storage medium as claimed in claim 10, wherein determining whether the distance between the person and the target is within an effective attention range based on the face candidate box comprises:

determining whether the face candidate box's height is not smaller than an effective face size;

determining the distance between the person and the target is within the effective attention range in response to detecting that the face candidate box's height not being smaller than the effective face size.

12. The non-transitory computer-readable storage medium as claimed in claim 11, wherein the effective face size is calculated by substituting the effective attention range and an FOV (field of view) into a second equation;

wherein the effective attention range is calculated by substituting the target's size into a first equation;

wherein the first equation and the second equation are obtained using a polynomial regression method based on a first history dataset and a second history dataset, respectively;

wherein the first history dataset comprises the correlation between a series of effective attention range and target's size;

wherein the second history dataset comprises the correlation between a series of effective face size, effective attention range, and FOV.

13. The non-transitory computer-readable storage medium as claimed in claim 10, wherein the keypoints of the face comprise a left-eye keypoint, a right-eye keypoint, a nose keypoint, a left-lips keypoint, and a right-lips keypoint.

14. The non-transitory computer-readable storage medium as claimed in claim 13, wherein the frontal determination process comprises:

determining whether the nose keypoint is in a circle;

determining that the face is frontal if the nose keypoint is in the circle;

wherein the center of the circle is the crossing point of the first straight line between the left-eye keypoint and the right-lips keypoint and the second straight line between the right-eye keypoint and the left-lips keypoint, and the radius of the circle equals the result of a predetermined ratio multiplies the sum of the height of the face candidate box and the width of the face candidate box.

15. The non-transitory computer-readable storage medium as claimed in claim 14, wherein the focus-of-attention calculation process comprises:

normalizing the circle so that the diameter of the circle is represented by 1 unit length;

mapping a first location of the nose keypoint in the normalized circle to a second location in a second image corresponding to the target;

wherein the second location is the focus of attention.

16. The non-transitory computer-readable storage medium as claimed in claim 15, wherein the first location and the second location are represented in the form of a Cartesian coordinate system; and wherein mapping the first location of the nose keypoint in the normalized circle to the second location in a second image corresponding to the target comprises using the following formula:

$$x = w\left(1/2\sqrt{2+u^2-v^2+2u\sqrt{2}} - 1/2\sqrt{2+u^2-v^2+2u\sqrt{2}}\right)$$

$$y = h\left(1/2\sqrt{2-u^2+v^2+2v\sqrt{2}} - 1/2\sqrt{2-u^2+v^2-2v\sqrt{2}}\right)$$

wherein (x, y) are the coordinates of the second location, (u, v) are the coordinates of the first location, w is the width of the target, and h is the height of the target.

17. The non-transitory computer-readable storage medium as claimed in claim 10, wherein the effective-attention-period calculation process comprises:

obtaining a face picture by cropping the first image based on the face candidate box;

obtaining a feature vector of the face picture by inputting the face picture into an AI (artificial intelligence) facial recognition model;

calculating an inner product value of the feature vector and a previous feature vector, which is obtained from a previous face picture in a previous first image at a previous time point;

determining whether the face picture and the previous face picture belong to the same person based on the inner product value;

calculating the effective attention period for the person to the target based on a series of time points corresponding to a series of face pictures belonging to the same person.

18. The non-transitory computer-readable storage medium as claimed in claim 10, wherein the program is loaded by the computer to further execute:

causing the processor to verify whether the face is effectively paying attention to the target by using a machine learning classification model based on the facial attributes and a plurality of target attributes of the target, in response to the effective attention period not being shorter than the period threshold;

wherein performing the focus-of-attention calculation process based on the target's size, the keypoints, and the face candidate box after determining that the effective attention period is not shorter than a period threshold comprises:

performing the focus-of-attention calculation process based on the target's size, the keypoints, and the face candidate box in response to the face being effective.

* * * * *